(12) United States Patent
Mizuno (10) Patent No.: US 9,848,759 B2
(45) Date of Patent: Dec. 26, 2017

(54) COIL STRUCTURE USED IN ENDOSCOPE AND ENDOSCOPE AND TREATMENT INSTRUMENT INCLUDING COIL STRUCTURE

(71) Applicant: OLYMPUS CORPORATION, Tokyo (JP)

(72) Inventor: Masahiro Mizuno, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/929,606

(22) Filed: Nov. 2, 2015

(65) Prior Publication Data

US 2016/0058271 A1 Mar. 3, 2016

Related U.S. Application Data

(63) Continuation of application No. PCT/JP2015/057366, filed on Mar. 12, 2015.

(30) Foreign Application Priority Data

Jun. 6, 2014 (JP) .................................. 2014-117941

(51) Int. Cl.
*A61B 1/00* (2006.01)
*A61B 1/005* (2006.01)
(Continued)

(52) U.S. Cl.
CPC ............ *A61B 1/0057* (2013.01); *A61B 1/005* (2013.01); *A61B 1/0011* (2013.01);
(Continued)

(58) Field of Classification Search
CPC ............ A61B 1/00087; A61B 1/00071; A61B 1/00073; A61B 1/00075; A61B 1/00078;
(Continued)

(56) References Cited

U.S. PATENT DOCUMENTS 5,460,168 A 10/1995 Masubuchi et al.
2001/0044570 A1\* 11/2001 Ouchi ................ A61B 1/00098
600/107

(Continued)

FOREIGN PATENT DOCUMENTS

EP 1 454 588 A2 9/2004
EP 2 612 608 A1 7/2013
(Continued)

OTHER PUBLICATIONS

Extended Supplementary European Search Report dated Jan. 11, 2017 in related European Patent Application No. 15 78 5042.1.

*Primary Examiner* — Ryan Henderson
(74) *Attorney, Agent, or Firm* — Scully, Scott, Murphy & Presser, P.C.

(57) ABSTRACT

A coil structure used in an endoscope includes a coil tube formed by densely winding a wire rod, both ends of the coil tube being fixed, a first contact surface formed on one surface of the wire rod on a distal end side, and a second contact surface formed on the other surface of the wire rod on a proximal end side, the first contact surface coming into contact with the second contact surface. The first contact surface is formed as a convex curved surface arcuate in cross section, a curvature center of which is located further on an inner side than an outer circumferential portion of the coil tube. For the convex curved surface, a curvature radius larger than a radius of the coil tube and smaller than a curvature radius during maximum bending of an insertion section is set.

10 Claims, 7 Drawing Sheets

(51) Int. Cl.
*A61B 1/018* (2006.01)
*A61B 17/00* (2006.01)
*A61M 25/00* (2006.01)
*A61M 25/01* (2006.01)

(52) U.S. Cl.
CPC .......... *A61B 1/00098* (2013.01); *A61B 1/018* (2013.01); *A61M 25/0138* (2013.01); *A61B 1/0055* (2013.01); *A61B 2017/0034* (2013.01); *A61B 2017/00305* (2013.01); *A61B 2017/00323* (2013.01); *A61M 25/0009* (2013.01); *A61M 25/0147* (2013.01)

(58) Field of Classification Search
CPC ... A61B 1/00098; A61B 1/005; A61B 1/0051; A61B 1/0052; A61B 1/0053; A61B 1/0055; A61B 1/0056; A61B 1/0057; A61B 1/0058; A61B 1/008; A61B 1/01; A61B 1/018; A61B 2017/00234; A61B 2017/00292; A61B 2017/00296; A61B 2017/0034; A61B 2017/003; A61B 2017/00305; A61B 2017/00309; A61B 2017/00314; A61B 2017/00318; A61B 2017/00323; A61B 2017/00327; A61B 2017/00331; A61B 2017/00358; A61M 25/0102; A61M 25/0133; A61M 25/0136; A61M 25/0138; A61M 25/0141; A61M 25/0144; A61M 25/0147; A61M 25/0152; A61M 25/0155; A61M 25/0158; A61M 25/0009; A61M 25/0012; A61M 25/005; A61M 25/0051; A61M 25/0052; A61M 25/0053; A61M 25/09; A61M 2025/015; A61M 2025/0161; A61M 2025/0163; A61M 2025/09058; A61M 2025/09066; A61M 2025/09075; A61M 2025/09083; A61M 2025/09091; A61M 2025/09133; A61M 2025/09191
USPC ........................ 600/104, 106, 107, 139–142; 604/523–528; 606/205–209
See application file for complete search history.

(56) References Cited

U.S. PATENT DOCUMENTS

| | | |
|---|---|---|
| 2004/0243108 A1 | 12/2004 | Suzuki |
| 2007/0233043 A1 | 10/2007 | Dayton et al. |
| 2008/0051694 A1 | 2/2008 | Kato |
| 2013/0190560 A1* | 7/2013 | Kaneko ................ A61B 1/0011 600/104 |

FOREIGN PATENT DOCUMENTS

| | | | |
|---|---|---|---|
| JP | S57-59519 A | 4/1982 | |
| JP | H05-115431 A | 5/1993 | |
| JP | H06-319682 A | 11/1994 | |
| JP | H07-194524 A | 8/1995 | |
| JP | H08-131550 A | 5/1996 | |
| JP | 2004-261463 A | 9/2004 | |
| JP | 2005-312564 A | 11/2005 | |
| WO | WO 2013038813 A1 * | 3/2013 | ........... A61B 1/0011 |

* cited by examiner

COIL STRUCTURE USED IN ENDOSCOPE AND ENDOSCOPE AND TREATMENT INSTRUMENT INCLUDING COIL STRUCTURE

CROSS REFERENCE TO RELATED APPLICATION

This application is a continuation application of PCT/JP2015/057366 filed on Mar. 12, 2015 and claims benefit of Japanese Application No. 2014-117941 filed in Japan on Jun. 6, 2014, the entire contents of which are incorporated herein by this reference.

BACKGROUND OF THE INVENTION

1. Field of the Invention

The present invention relates to a coil structure such as a coil sheath disposed in an endoscope or a coil sheath of a treatment instrument inserted through a treatment instrument channel of the endoscope and relates to the endoscope and the treatment instrument including the coil structure.

2. Description of the Related Art

Conventionally, in order to observe a part where it is difficult to observe an inside of a subject such as an interior of a body of an organism or a structure, an endoscope introducible into the subject has widely been used in, for example, a medical field or an industrial field.

For such an endoscope, for example, Japanese Patent Application Laid-Open Publication No. 5-115431 discloses a technique of a treatment instrument raising base for varying a direction of a treatment instrument or the like projected from a distal end portion of an insertion section. The treatment instrument raising base provided in a conventional endoscope is raised and lowered according to towing and relaxing of an operation wire provided in the insertion section.

Note that the operation wire is connected to an operation lever or the like provided in an operation section for remotely operating the treatment instrument raising base and is inserted into a densely wound coil pipe in the insertion section. The densely wound coil pipe is provided in order to suppress shrinkage of the insertion section due to the towing of the operation wire.

SUMMARY OF THE INVENTION

A coil structure used in an endoscope according to an aspect of the present invention includes: a coil tube disposed in or inserted into an insertion section of the endoscope, and formed by densely winding a wire rod, both ends of the coil tube being fixed; a first contact surface formed on one surface of the wire rod on a distal end side of the coil tube; and a second contact surface formed on another surface of the wire rod on a proximal end side of the coil tube, the first contact surface coming into contact with the second contact surface. The first contact surface is formed as a convex curved surface arcuate in cross section, a curvature center of which is located further on an inner side than an outer circumferential portion of the coil tube. For the convex curved surface, a curvature radius larger than a radius of the coil tube and smaller than a curvature radius during maximum bending of the insertion section is set.

An endoscope according to an aspect of the present invention is an endoscope in which a coil structure used in the endoscope is provided in the insertion section, the coil structure including: a coil tube formed by densely winding a wire rod, both ends of the coil tube being fixed; a first contact surface formed on one surface of the wire rod on a distal end side of the coil tube; and a second contact surface formed on another surface of the wire rod on a proximal end side of the coil tube, the first contact surface coming into contact with the second contact surface. The first contact surface is formed as a convex curved surface arcuate in cross section, a curvature center of which is located further on an inner side than an outer circumferential portion of the coil tube. For the convex curved surface, a curvature radius larger than a radius of the coil tube and smaller than a curvature radius during maximum bending of the insertion section is set.

A treatment instrument according to an aspect of the present invention is a treatment instrument in which a coil structure used in an endoscope is provided in a sheath, the coil structure including: a coil tube formed by densely winding a wire rod, both ends of the coil tube being fixed; a first contact surface formed on one surface of the wire rod on a distal end side of the coil tube; and a second contact surface formed on another surface of the wire rod on a proximal end side of the coil tube, the first contact surface coming into contact with the second contact surface. The first contact surface is formed as a convex curved surface arcuate in cross section, a curvature center of which is located further on an inner side than an outer circumferential portion of the coil tube. For the convex curved surface, a curvature radius larger than a radius of the coil tube and smaller than a curvature radius during maximum bending of the insertion section is set.

According to the present invention described above, it is possible to provide a coil structure used in an endoscope that can suppress occurrence of axis misalignment, buckling, and the like of a densely wound coil pipe and provide the endoscope and a treatment instrument including the coil structure.

DETAILED DESCRIPTION OF THE PREFERRED EMBODIMENT

A preferred mode of the present invention is described below with reference to the drawings. Note that, in the respective figures used in the following description, scales are varied for each of components to show the respective components in recognizable sizes on the drawings. The present invention is not limited only to numbers of the components, shapes of the components, ratios of sizes of the components, and relative positional relations among the respective components shown in the figures. In the following description, upward and downward directions viewed on a paper surface of the figures are sometimes described as an upper part and a lower part of a component.

Figure 1:
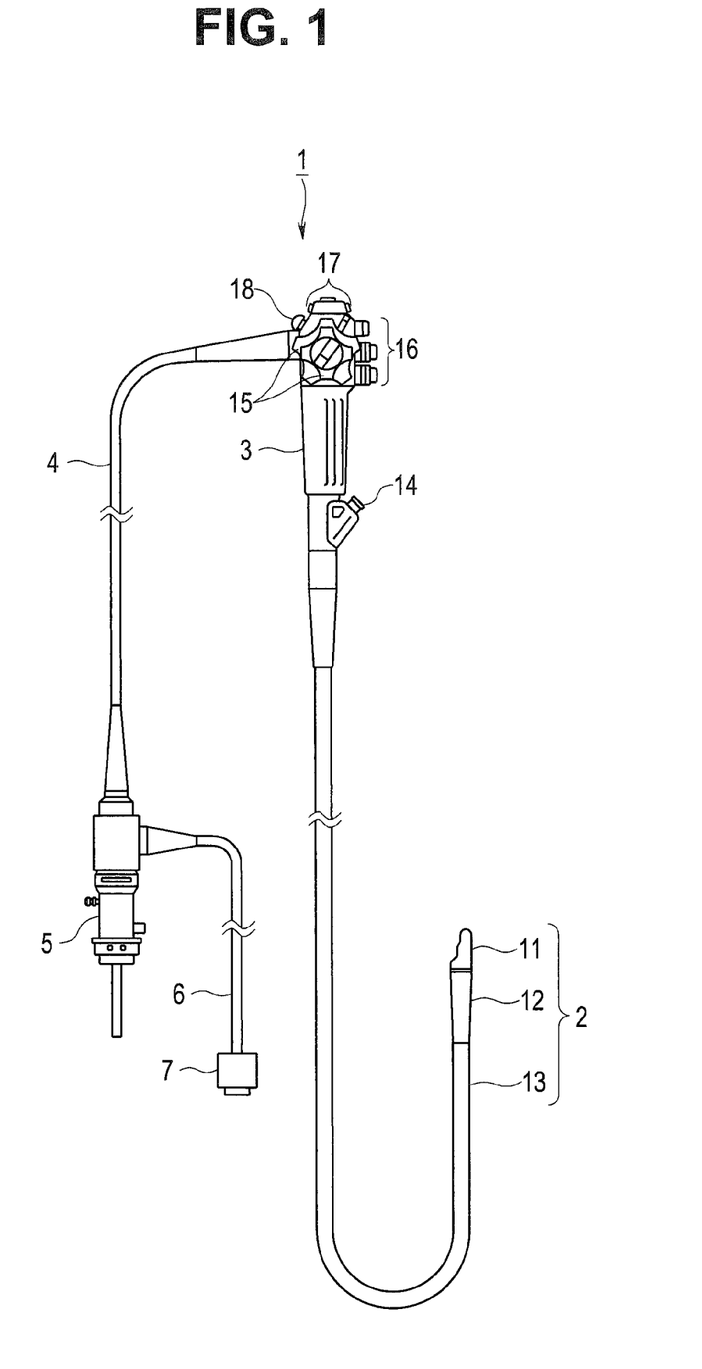
FIG. 1 is a diagram showing a configuration of an endoscope in an aspect of the present invention.
Figure 2:
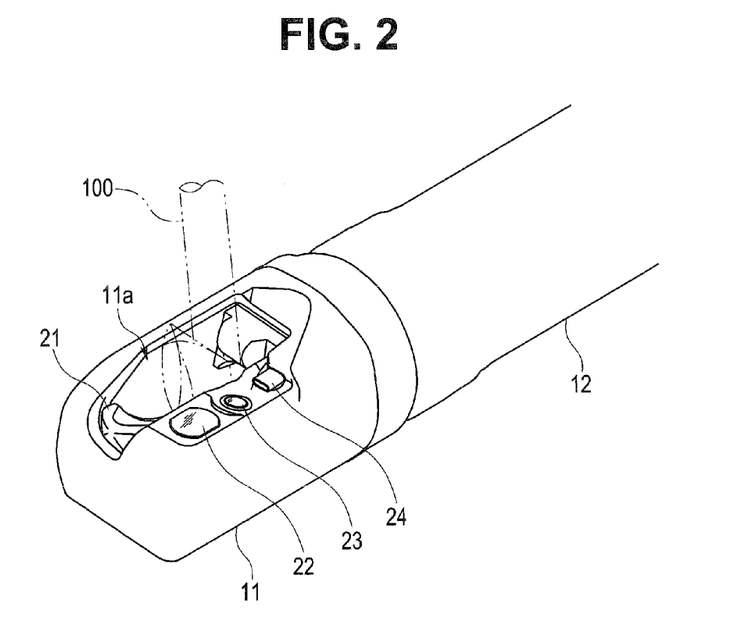
FIG. 2 is a perspective view showing a configuration of a distal end portion of an insertion section in the aspect of the present invention.
Figure 3:
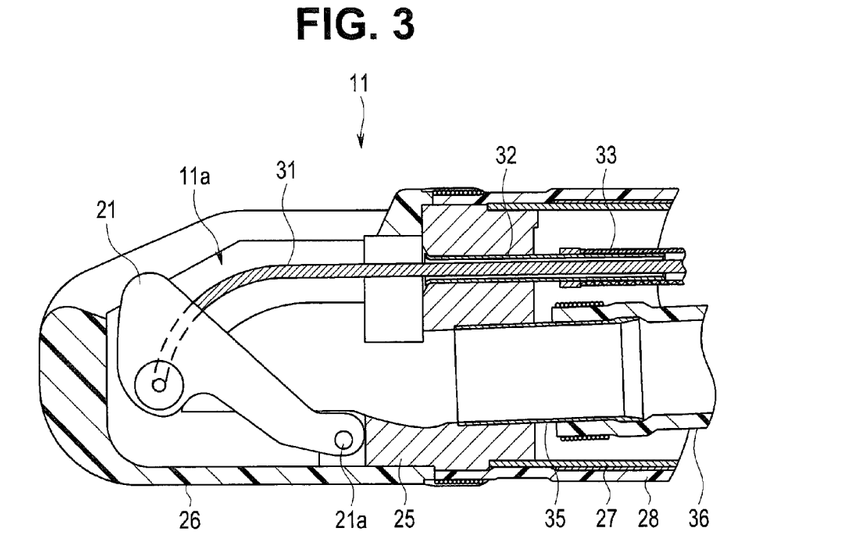
FIG. 3 is a sectional view showing the configuration of the distal end portion of the insertion section in the aspect of the present invention.
Figure 4:
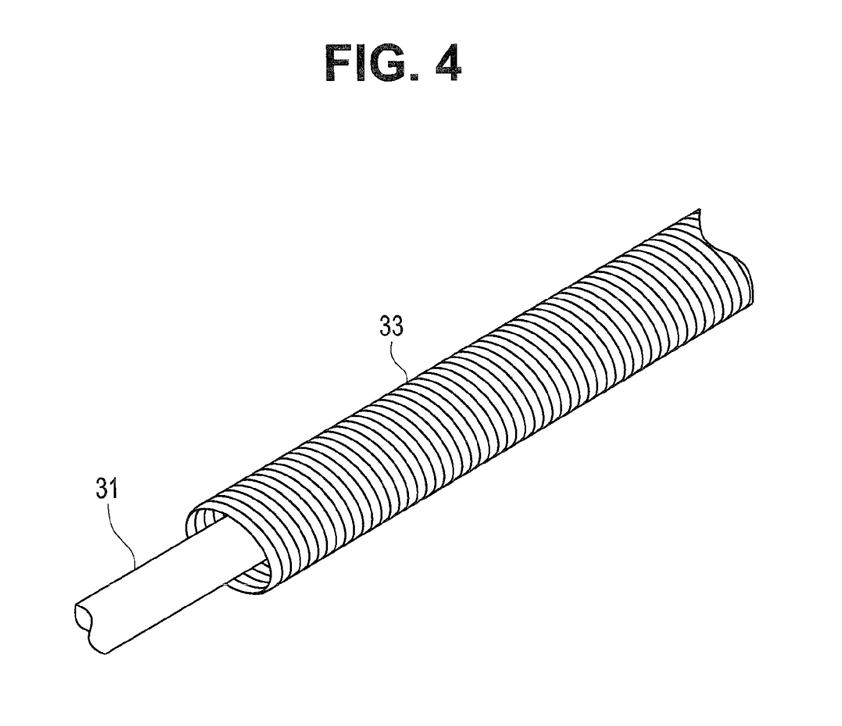
FIG. 4 is a perspective view showing a configuration of a densely wound coil tube through which an operation wire is inserted in the aspect of the present invention.
Figure 5:
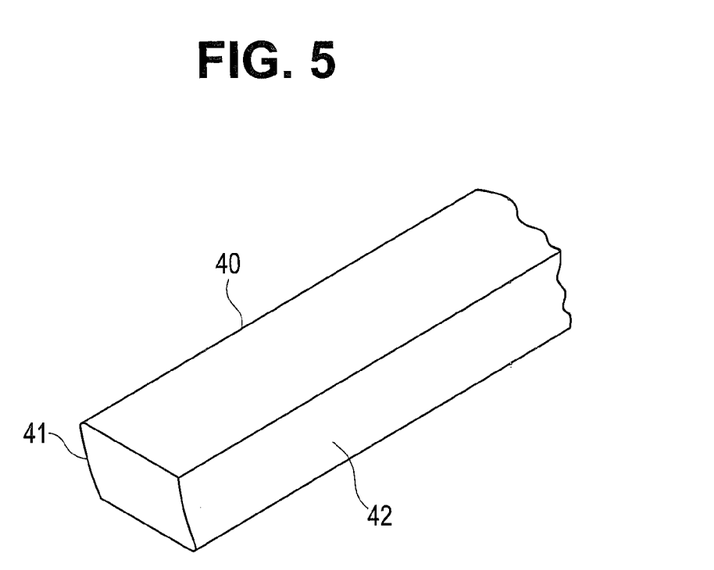
FIG. 5 is a perspective view showing a configuration of a wire rod which forms the densely wound coil tube in the aspect of the present invention.
Figure 6:
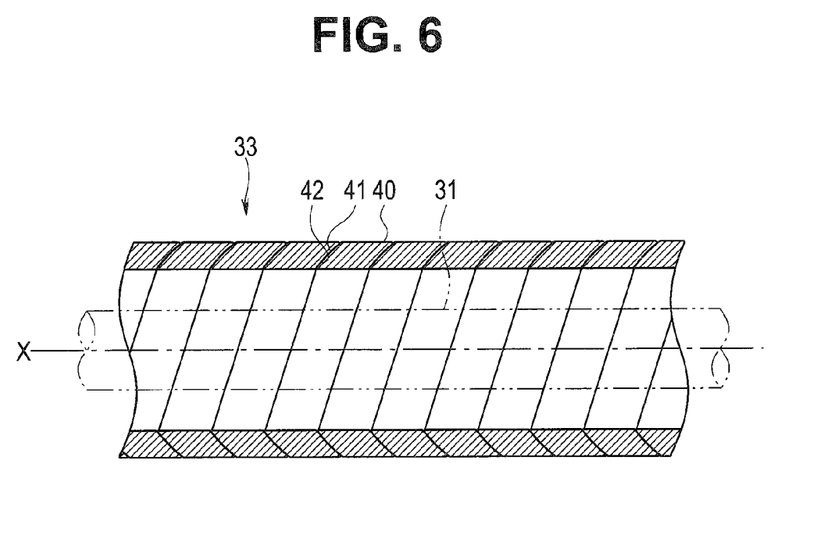
FIG. 6 is a partial sectional view showing the configuration of the densely wound coil tube through which the operation wire is inserted in the aspect of the present invention.
Figure 7:
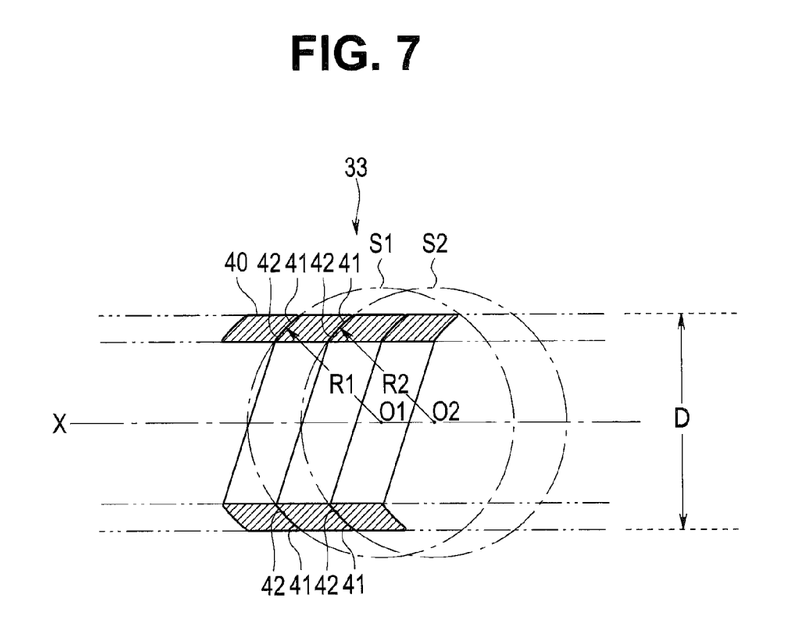
FIG. 7 is a partial sectional view for describing a configuration of a convex curved surface and a concave curved surface of the densely wound coil tube in the aspect of the present invention.
Figure 8:
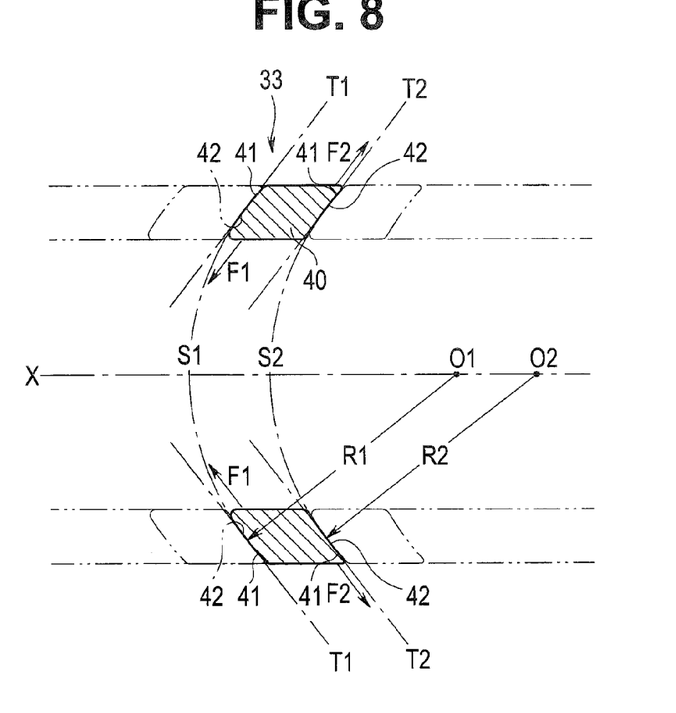
FIG. 8 is a partial sectional view for describing a state in which a compression force is generated in the densely wound coil tube in the aspect of the present invention.
Figure 9:
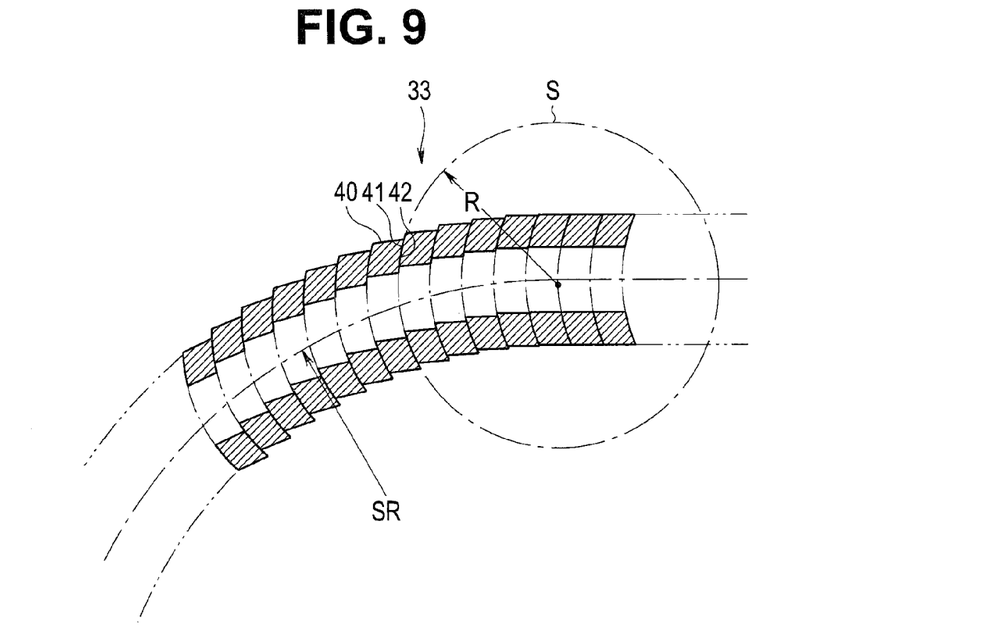
FIG. 9 is a partial sectional view of a state in which the densely wound coil tube is bent in the aspect of the present invention.
Figure 10:
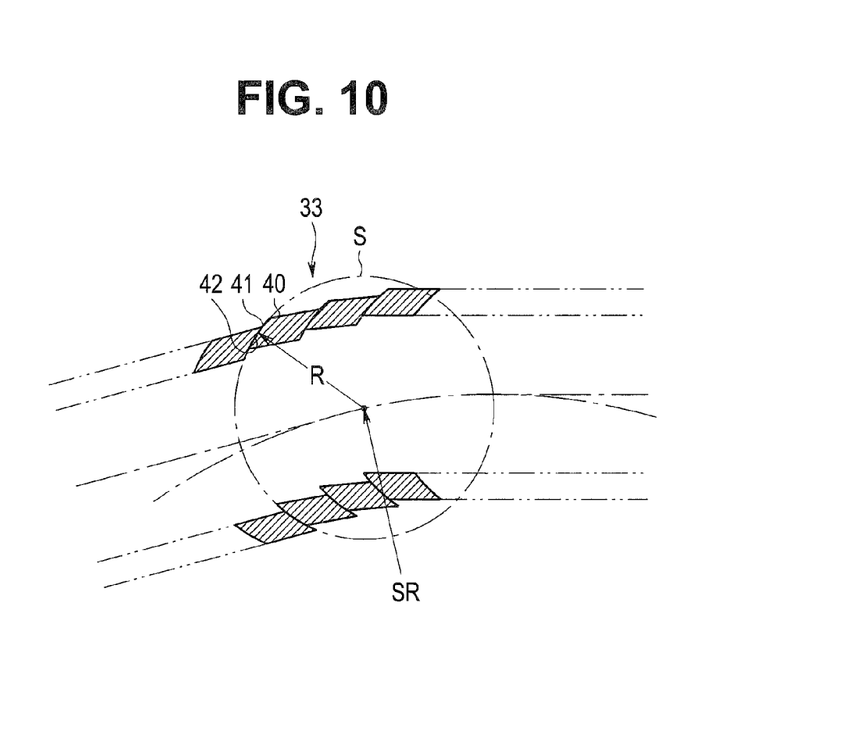
FIG. 10 is a partial sectional view for describing a relation between a curvature radius of the densely wound coil tube and a curvature radius of the convex curved surface and the concave curved surface in the aspect of the present invention.
Figure 11:
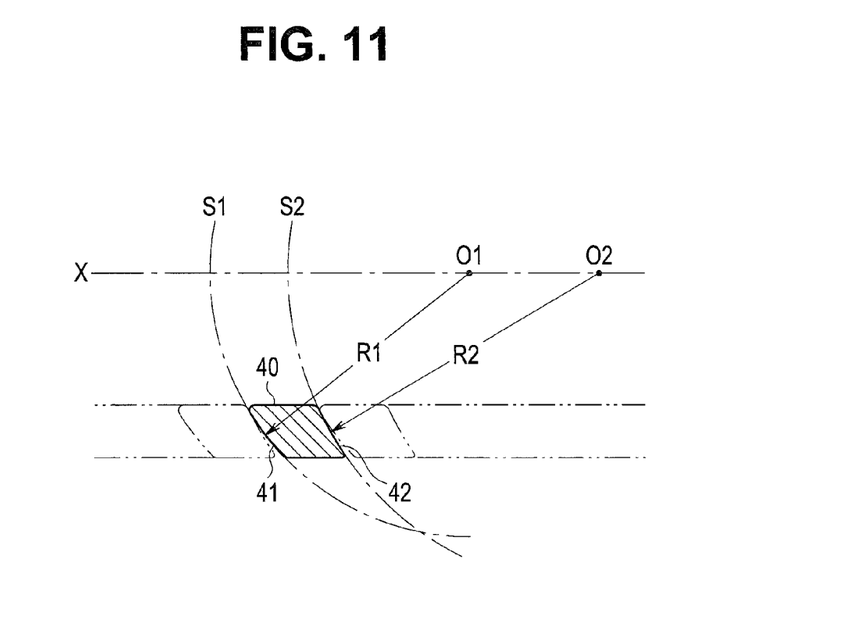
FIG. 11 is a partial sectional view for describing a configuration of a convex curved surface and a concave curved surface of a densely wound coil tube in a first modification of the aspect of the present invention.
Figure 12:
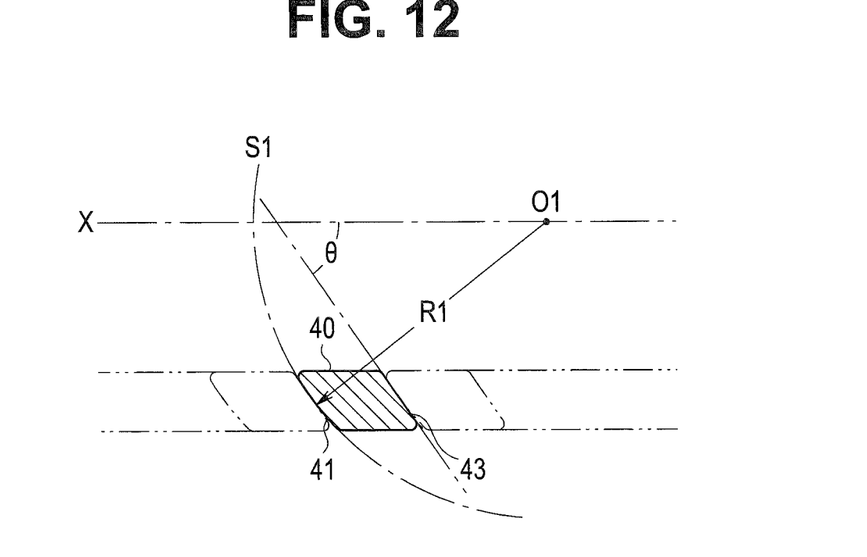
FIG. 12 is a partial sectional view for describing a configuration of a convex curved surface and a concave curved surface of a densely wound coil tube in a second modification of the aspect of the present invention.
Figure 13:
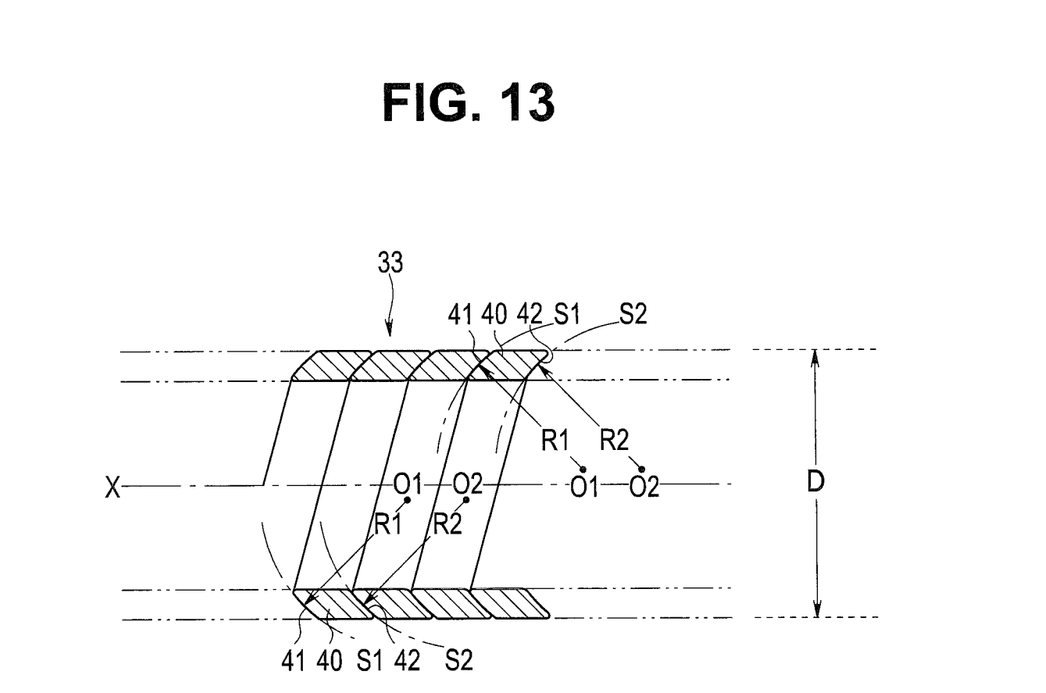
FIG. 13 is a partial sectional view for describing a configuration of a convex curved surface and a concave curved surface of a densely wound coil tube in a third modification of the aspect of the present invention.

Note that FIG. 1 is a diagram showing a configuration of an endoscope in an aspect of the present invention. FIG. 2 is a perspective view showing a configuration of a distal end portion of an insertion section. FIG. 3 is a sectional view showing the configuration of the distal end portion of the insertion section. FIG. 4 is a perspective view showing a configuration of a densely wound coil tube through which an operation wire is inserted. FIG. 5 is a perspective view showing a configuration of a wire rod which forms the densely wound coil tube. FIG. 6 is a partial sectional view showing the configuration of the densely wound coil tube through which the operation wire is inserted. FIG. 7 is a partial sectional view for describing a configuration of a convex curved surface and a concave curved surface of the densely wound coil tube. FIG. 8 is a partial sectional view for describing a state in which a compression force is generated in the densely wound coil tube. FIG. 9 is a partial sectional view of a state in which the densely wound coil tube is bent. FIG. 10 is a partial sectional view for describing a relation between a curvature radius of the densely wound coil tube and a curvature radius of the convex curved surface and the concave curved surface. FIG. 11 is a partial sectional view for describing a configuration of a convex curved surface and a concave curved surface of a densely wound coil tube in a first modification. FIG. 12 is a partial sectional view for describing a configuration of a convex curved surface and a concave curved surface of a densely wound coil tube in a second modification. FIG. 13 is a partial sectional view for describing a configuration of a convex curved surface and a concave curved surface of a densely wound coil tube in a third modification.

First, a schematic configuration of an endoscope 1 in the present embodiment is described with reference to FIG. 1 and FIG. 2. Note that a form is illustrated in which the endoscope 1 in the present embodiment optically observes an inside of a subject and includes a treatment instrument raising base at a distal end portion. However, a form may be adopted in which the endoscope 1 further includes an ultrasound probe at the distal end portion and scans an ultrasound beam in the subject to thereby pick up an ultrasound tomographic image of the subject.

The endoscope 1 mainly includes an insertion section 2 insertable into the inside of the subject, an operation section 3 located at a proximal end of the insertion section 2, and a universal cord 4 extending from a side portion of the operation section 3.

The insertion section 2 is configured by concatenating a distal end portion 11 disposed at a distal end, a bendable bending section 12 disposed on a proximal end side of the distal end portion 11, a flexible tube section 13 having flexibility disposed on a proximal end side of the bending section 12 and connected to a distal end side of the operation section 3.

In the operation section 3, besides a conduit cap 14 that communicates with a treatment instrument channel, an angle knob 15 for operating bending of the bending section 12, buttons 16 such as an air/water feeding button for performing control of a delivering operation of fluid from a fluid delivering section (not shown in the figure) provided at the distal end portion 11, switches 17 such as a release switch provided at the distal end portion 11, and an operation lever 18 for raising and lowering a treatment instrument raising base 21 (see FIG. 2) provided at the distal end portion 11 are provided.

The treatment instrument raising base 21 provided at the distal end portion 11 of the insertion section 2 raises and lowers a treatment instrument 100 (see FIG. 2), which projects from an opening portion 11a provided in a side circumferential portion of the distal end portion 11, to change a projecting direction. That is, the endoscope 1 is a so-called side-view type endoscope in which an illumination window 22, an observation window 23, and the like are provided in the side circumferential portion of the distal end portion 11 and the treatment instrument raising base 21 that raises the treatment instrument 100 in an observation direction is provided. Note that, at the distal end portion 11, an air/water feeding nozzle 24 for, for example, mainly cleaning the observation window 23 is provided.

At a proximal end portion of the universal cord 4, an endoscope connector 5 connected to a not-shown light source device is provided. Illumination light emitted from the light source device is transmitted through the universal cord 4, and a not-shown light guide bundle inserted through the operation section 3 and the insertion section 2 and is emitted from an illumination window 22 (see FIG. 2) provided at the distal end portion 11. Note that the endoscope 1 may include a light source such as an LED at the distal end portion 11 as an illumination device.

A video cable 6 is extended from the endoscope connector 5. A video connector 7 is provided at an end portion of the video cable 6. The video connector 7 is electrically connected to a not-shown camera control unit.

The camera control unit is electrically connected to, via the video connector 7, an image pickup device provided at the distal end portion 11. The camera control unit is electrically connected to a not-shown image display device and outputs, to the not-shown image display device, an image picked up by the image pickup device from the observation window 23 (see FIG. 2) provided at the distal end portion 11.

Next, a configuration of the distal end portion 11 of the insertion section 2 of the endoscope 1 is briefly described with reference to FIG. 3.

The distal end portion 11 of the insertion section 2 of the endoscope 1 includes a distal end rigid portion 25 functioning as a distal end portion main body. A distal end cover 26 is provided to cover the distal end rigid portion 25. A rigid tube 27 functioning as a first bending piece of the bending section 12 is connected to a proximal end side of the distal end rigid portion 25. Bending rubber 28 is provided halfway in the distal end rigid portion 25 to cover the rigid tube 27. Note that the bending rubber 28 covers the entire bending section 12.

A treatment instrument channel connection tube 35 is fit with the distal end rigid portion 25. A treatment instrument channel 36, which is a flexible tube body, is connected to a proximal end of the treatment instrument channel connection tube 35. The treatment instrument channel 36 is a tubular member having an inner diameter through which a treatment instrument can be inserted. The treatment instrument channel 36 is inserted through the insertion section 2. A proximal end of the treatment instrument channel 36 is connected to the conduit cap 14 of the operation section 3.

The treatment instrument raising base 21 is turnably axially supported by the distal end rigid portion 25 and a shaft member 21a. An operation wire 31 is connected to the treatment instrument raising base 21. The operation wire 31 is towed and relaxed according to a predetermined operation input of the operation lever 18 of the operation section 3. The treatment instrument raising base 21 is thus raised and lowered.

Note that the operation wire 31 is inserted through a metal tube 32 fit with the distal end rigid portion 25 and is further inserted through a densely wound coil tube 33 functioning as a densely wound coil pipe shown in FIG. 4 connected to a proximal end of the metal tube 32. Note that the densely wound coil tube 33 is inserted through the insertion section 2 and the operation section 3. A distal end of the densely wound coil tube 33 is fixed to the metal tube 32. A proximal end of the densely wound coil tube 33 is fixed in the operation section 3.

A detailed configuration of the densely wound coil tube 33 including the coil structure used in the endoscope 1 in the present embodiment is now described below with reference to FIG. 4 to FIG. 10.

The densely wound coil tube 33 shown in FIG. 4 is a tube body formed by winding, in a spiral shape, a metal wire 40, which is an elongated wire rod having a substantially trapezoidal shape in cross section, on a side surface of which a convex curved surface 41 and a concave curved surface 42 are formed as shown in FIG. 5, such that the convex curved surface 41 and the concave curved surface 42 are in surface contact with each other.

Note that the densely wound coil tube 33 is formed by winding the metal wire 40 such that, as shown in FIG. 6, in sectional shapes, the convex curved surface 41 is located on a distal end side in the densely wound coil tube 33 and the concave curved surface 42 is located on a proximal end side in the densely wound coil tube 33.

The convex curved surface 41 and the concave curved surface 42 of the metal wire 40 configure contact surfaces in the coil structure used in the endoscope 1. Note that the metal wire 40 is chamfered in an arcuate shape (an R shape) at a corner portion in a sectional direction. However, the metal wire 40 is not limited to this and may be configured to be not chamfered.

In the densely wound coil tube 33 configured in this way, as shown in FIG. 7, the sectional shapes of the convex curved surface 41 and the concave curved surface 42 of the windingly formed metal wire 40 are arcuate shapes. When curvature centers O1 and O2 of arcs of the convex curved surface 41 and the concave curved surface 42 are in a linear state, the curvature centers O1 and O2 are located on a center axis X.

That is, the sectional shape of the convex curved surface 41 on a distal end side in the densely wound coil tube 33 in the linear state is a part of an arc of an imaginary circle S1 indicated by an alternate long and short dash line of the curvature center O1 on the center axis X of the densely wound coil tube 33.

The sectional shape of the concave curved surface 42 on a proximal end side in the densely wound coil tube 33 in the linear state is a part of an arc of an imaginary circle S2 indicated by an alternate long and short dash line of the curvature center O2 on the center axis X of the densely wound coil tube 33.

Curvature radiuses R1 and R2 of the two imaginary circles S1 and S2 are the same (R1=R2). That is, the sectional shapes of the convex curved surface 41 and the concave curved surface 42 are arcuate shapes having the same curvature radiuses R1 and R2.

The convex curved surface 41 and the concave curved surface 42 in surface contact in a front-back direction along the center axis X are formed in arcuate shapes present in the same quadrant of the two imaginary circles S1 and S2. That is, in the convex curved surface 41 and the concave curved surface 42, parts above the center axis X on a paper surface of FIG. 7 are arcs in a second quadrant of the imaginary circles S1 and S2 and parts below the center axis X are arcs in a third quadrant of the imaginary circles S1 and S2.

A left side on the paper surface of FIG. 7 is the distal end side of the densely wound coil tube 33. The densely wound coil tube 33 is formed in an arcuate shape in which an inner diameter side of the convex curved surface 41 projects in a distal end direction and an outer diameter side of the concave curved surface 42 projects in a proximal end direction.

Note that, in the convex curved surface 41 and the concave curved surface 42, in any state of the densely wound coil tube 33 in the linear state, the curvature radiuses R1 and R2 of the arcuate shapes are set such that the respective curvature centers O1 and O2 are located within a range of a diameter D of the densely wound coil tube 33.

In other words, the curvature radiuses R1 and R2 of the arcs, which are the sectional shapes of the convex curved surface 41 and the concave curved surface 42, are set such that the respective curvature centers O1 and O2 are always located further on an internal side than an outer circumferential portion of the densely wound coil tube 33.

Further, the respective curvature radiuses R1 and R2 of the convex curved surface 41 and the concave curved surface 42 are set larger than a radius (D/2) of the densely wound coil tube 33.

In the densely wound coil tube 33 including the coil structure used in the endoscope 1 in the present embodiment configured as described above, both ends are fixed. Therefore, according to an increase in raising power of the treatment instrument raising base 21, a towing force of the operation wire 31 inserted through an inside increases and a compression force in an axial direction increases.

At this point, in the densely wound coil tube 33, as shown in FIG. 8, since the convex curved surface 41 and the concave curved surface 42 are in surface contact, a force acting on the convex curved surface 41 works in an inner circumferential direction and a force acting on the concave curved surface 42 side works in an outer circumferential direction along tangents T1 and T2 directions of respective arcuate portions (the imaginary circles S1 and S2). That is, in the densely wound coil tube 33, a force F1 of the convex curved surface 41 side on the distal end side moving in the inner diameter direction and a force F2 of the concave curved surface 42 side on the proximal end side moving in the outer diameter direction are balanced. Therefore, axis misalignment and the like are suppressed.

In the densely wound coil tube 33, as shown in FIG. 9, the convex curved surface 41 and the concave curved surface 42 bend while being in surface contact along the arcuate shapes of each other according to a bending shape of the bending section 12 or the flexible tube section 13 of the insertion section 2 of the endoscope 1. At this point, the densely wound coil tube 33 bends in a state in which parts of the convex curved surface 41 and the concave curved surface 42 are always in surface contact irrespective of an inner side and an outer side of the bending. Consequently, the densely wound coil tube 33 is bent in a state in which axis misalignment and the like are suppressed.

Note that, in the densely wound coil tube 33, as shown in FIG. 9 and FIG. 10, a curvature radius R of an arc (an imaginary circle S) in cross sections of the convex curved surface 41 and the concave curved surface 42 is set to be a curvature radius smaller than a curvature radius SR of bending of the bending section 12 and the flexible tube section 13 of the insertion section 2 (R<SR).

That is, in the densely wound coil tube 33, the curvature radius R of the arc in the cross sections of the convex curved surface 41 and the concave curved surface 42 is set to be smaller than the curvature radius (a minimum curvature radius) SR in a state in which the bending section 12 and the flexible tube section 13 of the insertion section 2 are bent to the maximum (R<SR).

Therefore, in a compressed state of the densely wound coil tube 33, even if the bending section 12 or the flexible tube section 13 of the insertion section 2 bends to the maximum and a bending angle increases, the convex curved surface 41 and the concave curved surface 42 are always in surface contact with each other. Therefore, sudden release of energy due to inability to withstand a compression force does not occur. Buckling and the like are also suppressed.

As described above, the densely wound coil tube 33 including the coil structure used in the endoscope 1 in the present embodiment is configured such that, even if the sturdy treatment instrument 100 or the like is raised by the treatment instrument raising base 21, which is the forceps raising base, provided at the distal end portion 11 of the endoscope 1, the towing force of the operation wire 31 inserted through the inside increases, and an excessive compression force is generated, axis misalignment can be suppressed because the force F1 of the convex curved surface 41 side moving in the inner diameter direction and the force F2 of the concave curved surface 42 side on the proximal end side moving in the outer diameter direction are offset.

Further, the densely wound coil tube 33 is configured such that, even if the bending section 12 or the flexible tube section 13 of the insertion section 2 is bent at a large angle, since at least parts of the convex curved surface 41 and the concave curved surface 42 are always in surface contact, buckling and the like can also be suppressed.

As a result, in the endoscope 1, since axis misalignment, buckling, and the like are suppressed in the densely wound coil tube 33, a situation is prevented in which desired reaction is not obtained in towing and relaxing of the operation wire 31 with respect to operation of the operation lever 18 or the operation wire 31 is caught and becomes inoperable.

First Modification

In the densely wound coil tube 33 in the present modification, as shown in FIG. 11, the convex curved surface 41 and the concave curved surface 42 of the metal wire 40 are set to have different curvature radiuses R1 and R2.

More specifically, in the densely wound coil tube 33 in the linear state, the sectional shape of the convex curved surface 41 on the distal end side is an arc of a part of the imaginary circle S1 having the curvature center O1 on the center axis X of the densely wound coil tube 33 and the sectional shape of the concave curved surface 42 on the proximal end side is an arc of a part of the imaginary circle S2 having the curvature center O2 on the center axis X of the densely wound coil tube 33.

The curvature radius R1 of the imaginary circle S1 is smaller than the curvature radius R2 of the imaginary circle S2 (R1<R2). That is, the sectional shape of the convex curved surface 41 is an arcuate shape having the curvature radius R1 smaller than the curvature radius R2 of the sectional shape of the concave curved surface 42.

Even such a configuration of the densely wound coil tube 33 including the coil structure used in the endoscope 1 has action and effects same as those described above. Axis misalignment, budding, and the like are suppressed in the densely wound coil tube 33 used in the endoscope 1.

Second Modification

In the densely wound coil tube 33 in the present modification, as shown in FIG. 12, the convex curved surface 41 on the distal end side is set to have the curvature radius R1. The proximal end side does not include the concave curved surface 42 and is formed as a plane 43 formed in a tangential direction of the arc (the imaginary circle S1), which forms the convex curved surface 41, and having a predetermined angle θ from the distal end side to the proximal end side with respect to the center axis X.

Even such a configuration of the densely wound coil tube 33 including the coil structure used in the endoscope 1 has action and effects same as those described above. Axis misalignment, buckling, and the like are suppressed in the densely wound coil tube 33 used in the endoscope 1.

Third Modification

The densely wound coil tube 33 in the present modification has a configuration in which, as shown in FIG. 13, both of the curvature centers O1 and O2 of the respective arcs (the imaginary circles S1 and S2) having the curvature radiuses R1 and R2, which form the convex curved surfaces 41 or the concave curved surfaces 42 of the metal wire 40, are not located on the center axis X.

In this way, the densely wound coil tube 33 has a configuration in which, in the densely wound coil tube 33 in the linear state, if the respective curvature centers O1 and O2 of the convex curved surfaces 41 and the concave curved surfaces 42 of the metal wire 40 are fit further on an internal side than the outer circumferential portion within a range of the diameter D, axis misalignment, buckling, and the like are suppressed.

Note that, in FIG. 13, the densely wound coil tube 33 has a configuration in which, across the center axis X of the densely wound coil tube 33, the convex curved surfaces 41 and the concave curved surfaces 42 of the metal wire 40 opposed to each other in a direction orthogonal to the center axis X have arcuate shapes having the same curvature radiuses (R1 and R2; R1=R2). However, without being limited thereto, but, as long as the respective curvature centers O1 and O2 are located in a region further on the internal side than the outer circumferential portion within the range of the diameter D of the densely wound coil tube 33, the convex curved surfaces 41 or the concave curved surfaces 42 opposed to each other in the direction orthogonal to the center axis X may be formed in arcuate shapes having different curvature radiuses. Further, the densely wound coil tube 33 may have a configuration in which the curvature radiuses R1 and R2 of the convex curved surfaces 41 and the concave curved surfaces 42 in the front-back direction along the center axis are different (R1≠R2).

Note that, as the coil structure used in the endoscope 1 described above, the densely wound coil tube 33 through which the operation wire 31 for raising and lowering the treatment instrument raising base 21 provided at the distal end portion 11 of the endoscope 1 is inserted, is illustrated. However, the coil structure can also be applied to, for example, a coil tube for hardness variation for varying hardness of the insertion section 2 of the endoscope 1 and a coil tube configuring a sheath of the treatment instrument 100 inserted into the treatment instrument channel 36 of the insertion section 2 of the endoscope 1.

The coil structure used in the endoscope 1 described above can also be applied to, for example, a coil provided in the insertion section 2 and contracted to change the hardness of the insertion section 2.

Further, the coil structure may be configured to insert therethrough a flexible shaft for transmitting a rotation driving force from a driving source such as a motor provided in the operation section 3 of the endoscope 1 to some driven member provided in the insertion section 2. Note that the coil structure itself may be used as a member for transmitting the rotation driving force.

The invention described in the respective embodiments described above is not limited to the embodiments and the modifications. Besides, in an implementation stage, various modifications can be carried out in a range not departing from the spirit of the invention. Further, inventions in various stages are included in the respective embodiments. Various inventions can be extracted according to appropriate combinations in a disclosed plurality of constituent features.

For example, even if some of the constituent features are eliminated from the entire constituent features shown in the respective embodiments, when the described problems can be solved and the described effects can be obtained, a constitution after eliminating some of the constituent features can be extracted as an invention.

What is claimed is:

1. A coil structure used in an endoscope, comprising:
a coil tube disposed in or inserted into an insertion section of the endoscope, and formed by densely winding a wire rod having a substantially quadrilateral shape in cross section, both ends of the coil tube being fixed, the coil tube having a plurality of loops formed by winding the wire rod; wherein
a first contact surface formed on one surface on a distal end side of each of the plurality of loops;
a second contact surface formed on another surface on a proximal end side of each of the plurality of loops, the first contact surface coming into contact with the second contact surface,
the first contact surface is formed as a convex curved surface arcuate in cross section, the convex curved surface having a radius of curvature with a center of curvature located within an internal lumen of the coil tube,
the second contact surface is formed as a concave curved surface arcuate in cross section, the concave curved surface having a radius of curvature with a center of curvature located within an internal lumen of the coil tube, and
the radius of curvature of the convex surface is larger than a radius of the coil tube and smaller than a radius of curvature of the insertion section of the endoscope when the insertion section is bent in a maximum state.

2. The coil structure used in the endoscope according to claim 1, wherein the radius of curvature of the concave curved surface is the same as the radius of curvature of the convex curved surface.

3. The coil structure used in the endoscope according to claim 1, wherein the radius of curvature of the convex curved surface is smaller than the radius of curvature of the concave curved surface.

4. The coil structure used in the endoscope according to claim 1, wherein the center of curvature of the convex curved surface and the center of curvature of the concave curved surface are located on a center axis of the coil tube when the coil tube is in a linear state.

5. The coil structure used in the endoscope according to claim 1, wherein an operation wire is inserted through an inside of the coil tube.

6. The coil structure used in the endoscope according to claim 1, wherein an operation wire for raising and lowering a treatment instrument raising base provided in the endoscope is inserted through the coil tube, and the coil tube is disposed in the insertion section of the endoscope.

7. The coil structure used in the endoscope according to claim 1, wherein the coil tube is disposed in the insertion section of the endoscope and contracted to change hardness of the insertion section.

8. The coil structure used in the endoscope according to claim 1, wherein the coil tube is driving force transmitting means to transmit a rotational force disposed in the insertion section of the endoscope.

9. The coil structure used in the endoscope according to claim 1, wherein a flexible shaft to transmit a rotational force disposed in the insertion section of the endoscope is inserted through an inside of the coil tube.

10. An endoscope comprising the coil structure used in the endoscope according to claim 1 in the insertion section.

* * * * *